United States Patent [19]
Holt et al.

[11] Patent Number: 5,962,282
[45] Date of Patent: Oct. 5, 1999

[54] PRODUCTION OF OPTICALLY ACTIVE 2-SUBSTITUTED TETRAHYDROPYRAN-4-ONES

[76] Inventors: Robert Antony Holt; Stuart Richard Rigby, both of PO Box 2, Belasis Avenue, Billingham, Cleveland TS23 1YN; David Waterson, Mereside, Alderley park, Macclesfield, Cheshire, SK10 4TG, all of United Kingdom

[21] Appl. No.: 09/077,192
[22] PCT Filed: Nov. 19, 1996
[86] PCT No.: PCT/GB96/02838
  § 371 Date: May 26, 1998
  § 102(e) Date: May 26, 1998
[87] PCT Pub. No.: WO97/19185
  PCT Pub. Date: May 29, 1997

[30] Foreign Application Priority Data

Nov. 23, 1995 [GB] United Kingdom .................... 9523924

[51] Int. Cl.$^6$ ...................................................... C12P 17/06
[52] U.S. Cl. ........................... 435/125; 435/197; 435/280
[58] Field of Search ..................................... 435/125, 197, 435/280

[56] References Cited

U.S. PATENT DOCUMENTS 5,395,766  3/1995  Koizumi et al. ......................... 435/280
5,527,916  6/1996  Blacker et al. ......................... 548/200

FOREIGN PATENT DOCUMENTS 93 06235  4/1993  WIPO .
93 06236  4/1993  WIPO .

OTHER PUBLICATIONS

Computer Abstract CEABA 97:6771890 Auartey et al "Selectivity enhancement of PPL–catalyzed resolution by enzyme fractionation and medium engineering: synthees of both enantiomers of tetrahydropyran–2–methanol" Enyme Microb. Technol (1996) 19(5) 361–366.

*Primary Examiner*—Herbert J. Lilling

[57] ABSTRACT

Optically active 2-substituted tetrahydropyran-4-ols or esters thereof may be prepared using esterases or hydrolases from the corresponding racemic mixtures of esters or alcohols. This provides a route to the corresponding optically active ketones.

The racemic mixtures are preferably in the cis-form. such mixtures may be produced by reacting but-3-ene-1-ol with an aldehyde in the presence of an acid.

14 Claims, No Drawings

PRODUCTION OF OPTICALLY ACTIVE 2-SUBSTITUTED TETRAHYDROPYRAN-4-ONES

This application is the national phase of international application PCT/GB96/02838 filed Nov. 19, 1996 which designated the U.S.

THIS INVENTION relates to a Process for the Production of Optically Active 2-Substituted tetrahydropyran-4-ones.

Certain tetrahydropyran-4-ones are of interest as chemical intermediates in the production of biologically active materials, for example those of European Patents 465,812; 462,813; 409,413; 420,511; 410,661; 385,662 and 375,404. In at least some cases compounds of enhanced activity are produced if the tetrahydropyran-4-one is 2-substituted and is in the (S) configuration. Compounds of the (R) configuration are of possible research interest.

This invention comprises a process of producing an optically active 2-substituted tetrahydropyran-4-ol or ester thereof which comprises stereospecifically esterifying a 2-substituted tetrahydropyran-4-ol using a stereospecific esterase or stereospecifically hydrolysing an ester thereof with a stereospecific hydrolase.

We have found that the invention may be carried out with surprisingly high stereo specificity.

If desired the hydrolysis of the ester product may be carried out using a stereospecific hydrolase in order to increase the optical purity further.

The cis 2-substituted tetrahydropyran-4-ols or esters react more readily in the invention than the trans compounds and the (R) compounds can be reacted stereospecifically both in esterification and hydrolysis thereby leaving the (S) compounds unconverted.

The racemic mixture of the 2-substituted tetrahydropyran-4-ol in substantially the cis form may be produced by reacting but-3-ene-1 ol with an aldehyde of formula X CHO in which X is the desired 2-substituent of the pyranol in the presence of an acid which is preferably sulphuric acid. X is suitably an alkyl for example, an ethyl or methyl group or a substituted alkyl for example mono or di fluoro-substituted alkyl for example methyl or ethyl group. A method for this process using $H_2SO_4$ as catalyst is described by Hanschke (Chem Ber (1955) vol 88 p 1053). Cis and trans orientations are lost on oxidation to the corresponding ketone but we have found the cis product to be very suitable for this invention.

The invention also comprises a process of producing an optically active 2-substituted tetrahydropyran-4-ol or ester thereof which comprises producing a cis-racemic 2-substituted tetrahydopyran-4 ol by reacting but-3-ene-1-ol with an aldehyde of formula XCHO in which X is the desired 2-substituent of the pyranol in the presence of an acid, esterifying the racemic mixture using a stereospecific esterase or esterifying the racemic mixture optionally non stereospecifically and hydrolysing it with a stereospecific hydrolase.

The esters may be made by normal methods, preferably using the free acids, acyl halides and/or anhydrides, in non stereospecific esterification. In stereospecific esterification it is preferred to transesterify with another ester, which is suitably a vinyl ester, as the by-product, acetaldehyde, is not involved in a back-reaction. It is preferred that the stereospecific esterification reaction and/or hydrolysis be carried out at a pH of 5 to 10, at least if excess water for example water of reaction, is present, more preferably 6 to 9, and a temperature of preferably 20 to 65° C., more preferably 25 to 50° C. The esters are preferably esters of lower alkanoic acids having 2 to 8 carbon atoms, benzoic acid or substituted derivatives thereof.

The enzymes may be provided as such or as whole cells comprising them. It is preferred that they be immobilised so as to facilitate their separation from the product and, if desired, re-use.

The stereospecific esterification and/or hydrolysis step(s) may be carried out by mixing the reactant(s) with the enzyme, normally in the presence of at least an amount of water sufficient to allow enzyme activity and, in the case of hydrolysis to supply the water of reaction and optionally an inert solvent.

Preferred enzymes include those from *Humicola lanuginosa* for example that sold under the Trade Mark Lipolase and Pseudomonas for example that sold under the Trade Mark SAM II and more preferably those from *Candida antarctica*, for example that sold under the Trade Mark NOVOZYM.

Oxidation of the alcohol to the ketone is suitably carried out with a strong oxidising agent, for example chromic acid suitably in the presence of a strong acid for example sulphuric acid and an inert organic solvent for example a ketone. The temperature is preferably in the range 0 to 40° C. for example 0 to 30° C.

If desired, the alcohol may be further reacted, for example by oxidation of the corresponding ketone in the presence of the ester. Any separation of the ester which is required may be carried out after such further reaction. The invention may be used as a route to either the product of the stereospecific reaction or to the unconverted isosmer.

EXAMPLE 1

Preparation of Racemic Cis-2-Methyltetrahydro-(4H)-Pyran-4-ol Butyrate Ester

Racemic cis-2-methyltetrahydro-(4H)-pyran-4-ol was prepared by the method of E Hanschke (Chemische Berichte (1955), volume 88, p 1053).

Typically esterification was carried out as follows.

A solution of cis-2-methyltetrahydro-(4H)-pyran-4-ol (20 g, 0.172 mole) and triethylamine (20.2 g, 0.20 mole) in dichloromethane (120 ml) was cooled in an ice bath. Butyryl chloride (18.1 g, 0.17 mole) was added slowly with stirring over 15 minutes. The ice bath was removed and the reaction stirred at room temperature for 3 hours. Water (100 ml) was added to the reaction mixture and the organic fraction recovered from the mixture. The organic phase was washed with dilute hydrochloric acid (75 ml, 2 molar), saturated aqueous sodium chloride (75 ml) and then dried over anhydrous magnesium sulphate. The solvent was removed under reduced pressure. The residue was distilled under reduced pressure to yield the butyrate ester (20. g, 64% yield; 60–73° C./5 mm Hg). The product contained approximately 5% of the trans isomer.

NMR ($CDCl_3$): 0.95 (3H, m), 1.15–2.05 (9H, m), 2.30 (2H, m), 3.45 (2H, m), 4.0 (1H, m), 4.85 (1H, m).

EXAMPLE 2

Identification of Enzymes Hydrolysing Cis-2-Methyltetrahydro-(4H)-Pyran-4-ol Esters Enantioselectively The enzymic hydrolysis of esters was carried out in a Mettler DL25 autotitrator to maintain the pH at the desired level. The extent of hydrolysis was conveniently calculated from the consumption of the titrant, sodium hydroxide.

The butyric ester (0.29 g) was suspended as droplets in a buffer (30 ml) of pH 7.5 comprising tris (hydroxymethyl) amino methane (10 mM), sodium chloride (60 mM) and calcium chloride (20 mM). To this was added enzyme (100 mg of solid or 2 ml when a liquid). The temperature was held at 30° C. and the reaction mixture stirred whilst pH was maintained by the automatic addition of aqueous sodium hydroxide (0.25 molar). A decrease in titration rate as hydrolysis approached 50% was used as an indication of enantioselectivity, promising reactions were extracted and analysed as follows. When the quantity of sodium hydroxide added was equivalent to the hydrolysis of 50% of the ester the reaction mixture was extracted with an equal volume of diethyl ether. Where immobilised enzyme was used this was removed by filtration prior to extraction with diethyl ether. The residual ester was recovered in the ether layer whilst the enzyme and the majority of the pyranol were present in the aqueous layer. The ether layer was washed with an equal volume of water to remove traces of pyranol from the organic layer. The diethyl ether fraction was dried over anhydrous sodium sulphate, the ether layer recovered by filtration and the butyric ester isolated from it by removal of the ether by distillation at reduced pressure.

The enantiomers of the butyric ester were measured by HPLC using a Chiralcel OB column, 250 mm×4.6 mm (Daicel Chemical Industries Ltd) eluted with hexane: 2-propanol (99:1) at a rate of 1 ml/minute. The ester was detected by UV absorption at 215 nm. Under these conditions the (2S, 4S) butyric ester eluted at 5.7 minutes whilst the (2R, 4R) butyric ester eluted at 7.2 minutes. The results of the enzyme screen are shown in Table 1.

TABLE 1

| Enzyme | Source | Hydrolysis | Ratio of Butyric Ester Enantiomers (S):(R) |
|---|---|---|---|
| Chromobacterium viscosum | B | Yes | nd |
| Pseudomonas fluorescens | B | Yes | nd |
| Mucor miehei | B | No | nd |
| Geotrichum candidum | B | No | nd |
| Candida cylindracea | B | Yes | nd |
| Porcine pancreatic lipase | B | No | nd |
| Porcine liver esterase | S | Yes | nd |
| Lipase P | A | Yes | 80:20 |
| Lipase SAM II | A | Yes | 80:20 |
| Lipolase ™ | N | Yes | >95:5 |
| Novozym 435 ™ | N | Yes | >95:5 | nd not determined.
B Biocatalysts Ltd, Main Avenue, Treforest Industrial Estate, Pontypridd CF37 5UT, United Kingdom.
S Sigma Chemical, Fancy Road, Poole, Dorset BH17 7BR, United Kingdom.
A Amano Pharmaceutical Co Ltd, Eschersheimer Landstrasse 49, D-6000, Frankfurt am Main 1, Germany.
N Novo Nordisk A/S, Novo alle, 2880 Bagsvaerd, Denmark.

EXAMPLE 3
Preparative Scale Resolution of 2-Methyltetrahydro-(4H)-Pyran-4-ol Butyrate Ester using Lipase from *Candida Antarctica* (NOVOZYM 435™) and conversion to (S)-2-Methyltetrahydro-(4H)-Pyran-4-one To a 10 liter stirred glass reaction vessel was added water (4 liters) and tris (hydroxymethyl) amino methane free base (4.84 g, 40 millimoles) to give a solution of pH 9.5. To this was added 2-methyltetrahydro-(4H)-pyran-4-ol butyrate ester (2.933 Kg, 15.77 moles) resulting in a decrease in pH to 5.0. The pH of the stirred biphasic mixture was adjusted to pH 8.0 with sodium hydroxide (5 molar). Enzyme (30 g of Novozym 435™ beads) was slurried in 100 ml of water and added to the reactor to start the reaction. The pH was controlled at pH 7.8–8.0 by the automatic addition of sodium hydroxide solution (5 molar), the temperature was controlled at 28–32° C.

After 25 hours the reaction mixture was filtered through a Whatman GF/B glass fibre filter to remove the enzyme beads. The filtrate was allowed to settle and the upper organic layer recovered. Pentane (500 ml) was added to the organic fraction which was then washed twice with deionised water (1 liter) to remove traces of pyranol from the organic fraction. The separated organic fraction was dried over anhydrous sodium sulphate and filtered. The filtrate was then distilled at reduced pressure to remove pentane yielding resolved (4S, 6S)-2-methyltetrahydro-(4H)-pyran-4-ol butyrate ester as a pale yellow oil. Ester recovered= 1.359 Kg (46% yield, 96% chemical strength).

A sample of the resolved 2-methyltetrahydro-(4H)-pyran-4-ol butyrate ester was hydrolysed to the corresponding alcohol as follows. Butyrate ester (627.8 g, 96% chemical strength) was added to a solution of sodium hydroxide (5 molar, 1200 ml) and the mixture warmed to 70° C. After 1.5 hours the mixture was cooled to room temperature and saturated aqueous sodium chloride (600 ml) was added. The mixture was extracted with diethyl ether (600 ml×11). The organic fractions were combined and dried over anhydrous magnesium sulphate, decolourised with charcoal and the solvent removed under reduced pressure to yield 2-methyltetrahydro-(4H)-pyran-4-ol (353.1 g, 94% yield).

NMR (CDCl$_3$): 1.21 (3H, d), 1.5 (2H, m), 1.9 (2H, m), 3.4 (2H, m), 3.78 (1H, m), 4.0 (1H, m).

A sample of the 2-methyltetrahydro-(4H)-pyran-4-ol was oxidised to 2-methyltetrahydro-(4H)-pyran-4-one under the following conditions. 2-methyltetrahydro-(4H)-pyran-4-ol (119 g) was added to acetone (2700 ml) and cooled to 8° C. on an ice bath. Chromic acid solution (234 ml, 8N-prepared by adding 266.7 g of chromium (VI) oxide to a mixture of 230 ml of concentrated sulphuric acid and 400 ml of water and made up to 1 liter with water) was added dropwise over 1 hour with rapid stirring. After a further 2 hours isopropanol (5 ml) was added gradually until the colour of the solution turned green. The acetone solution was decanted and filtered. The residue was washed with acetone. The combined filtrate and washings were distilled under reduced pressure to remove acetone, the aqueous residue was then extracted with diethyl ether (500 ml followed by 3×125 ml). The combined extracts were dried over magnesium sulphate and the diethyl ether removed under reduced pressure. The residue was distilled under reduced pressure to yield the pyranone (92.4 g, 79%, 60° C./80 mm Hg). NMR (CDCl$_3$): 1.31 (3H, d), 2.2–2.64 (4H, m), 3.69 (2H, m), 4.28 (1H, m).

The enantiomeric purity of 2-methyltetrahydro-(4H)-pyran-4-one was determined by chiral stationary phase HPLC using the conditions described in Example 2. The (S)-enantiomer eluted at 15.6 minutes whilst the (R)-enantiomer eluted at 18.1 minutes. The reaction product consisted of 98% (S)-enantiomer, 2% (R)-enantiomer.

EXAMPLE 4
Resolution of Racemic Cis-2-Methyltetrahydro-(4H)-Pyran-4-ol by Enantioselective Transesterification Catalysed by NOVOZYM 435™ in the presence of Vinyl Butyrate To 20 g of racemic cis-2-methyltetrahydro-(4H)-pyran-4-ol (0.172 mole) was added vinyl butyrate (14 g, 0.123 mole) and Novozym 435™ immobilised enzyme preparation (0.2 g). The reaction mixture was stirred at 28° C. The reaction was monitored for formation of butyrate ester and disappearance of pyranol by gas chromatography. Analysis was carried out using a Perkin-Elmer 8500 gas chromatograph fitted with a 30 meter×0.32 mm DB5 column (J & W Scientific). Helium (8 psi) was the carrier gas and detection was by flame ionisation. The temperature programme consisted of an initial 1 minute at 100° C. followed by an increase to 170° C. at a rate of 20° C./minute, the temperature was then maintained at 170° C. for 10 minutes. The retention time of cis-2-methyltetrahydro-(4H)-pyran-4-ol was 6.1 minutes whilst that for the corresponding butyrate ester was 12.1 minutes. The rate of reaction decreased as it approached 50% esterification and the reaction stopped after 12 hours at 52.5% esterification.

The solution was filtered to remove the enzyme beads and then the filtrate was extracted twice with an equal volume of water to remove unreacted cis-2-methyltetrahydro-(4H)-pyran-4-ol. The combined aqueous extracts were then back-extracted twice with an equal volume of pentane to remove any trace of butyrate ester from the aqueous phase. The aqueous solution containing the cis-2-methyltetrahydro-(4H)-pyran-4-ol was then saturated with sodium chloride and extracted twice with an equal volume of ethyl acetate. The ethyl acetate extract was dried over anhydrous sodium sulphate and the solvent removed by distillation under reduced pressure to yield resolved cis-2-methyltetrahydro-(4H)-pyran-4-ol (8.86 g).

The enantiomeric purity of the resolved cis-2-methyltetrahydro-(4H)-pyran-4-ol was determined by chiral stationary phase HPLC of the benzoyl ester. The benzoyl ester was synthesised as follows; To a 50 ml stoppered tube was added cis-2-methyltetrahydro-(4H)-pyran-4-ol (0.2 g, 1.724 m mole), benzoic anhydride (0.39 g, 1.725 m mole), pyridine (5 ml) and dimethylaminopyridine (5 mg). The mixture was incubated at 60° C. for 6 hours. The reaction mixture was cooled to room temperature, diluted to 50 ml with diethylether and washed successively with 2×50 ml hydrochloric acid (20 millimolar), sodium hydroxide (100 millimolar), distilled water and saturated aqueous sodium chloride. The organic layer was recovered, dried over anhydrous sodium sulphate and filtered. The filtrate was collected and the diethyl ether removed by distillation under reduced pressure to yield the benzoyl ester of cis-2-methyltetrahydro-(4H)-pyran-4-ol as a pale yellow oil.

The enantiomeric purity was determined using a Chiralcel OB column (Daicel Chemical Industries Ltd), 250 mm×4.6 mm, eluted with hexane:ethanol (99.5:0.5) at a rate of 0.75 ml/minute. The compounds were detected by UV absorption at 225 mm. The retention times for the (2R, 4R) and (2S, 4S) enantiomers of the benzoyl ester derivative of 2-methyltetrahydro-(4H)-pyran-4-ol were 17.1 minutes and 21.7 minutes respectively. Analysis of the resolved sample indicated the optical purity to be 98.5% (2S, 4S), 1.5% (2R, 4R).

EXAMPLE 5
Resolution of Racemic Cis-2-Methyltetrahydro-(4H)-Pyran-4-ol by Enantioselective Transesterification Catalysed by NOVOZYM 435™ in the presence of Vinyl Acetate To 2 g of racemic cis-2-methyltetrahydro-(4H)-pyran-4-ol (17.2 millimoles) was added 1.01 g of vinyl acetate (12.9 millimoles) and 0.1 g of immobilised enzyme preparation Novozym 435™. The reaction mixture was stirred at 28° C. and the reaction monitored by gas chromatography as described in Example 4. The retention time of the acetyl ester of cis-2-methyltetrahydro-(4H)-pyran-4-ol was 8.2 minutes. The reaction was halted when 58% of the pyranol had been converted to the acetyl ester (4 hours). The reaction mixture was processed as described in Example 4 to yield 0.57 g of resolved cis-2-methyltetrahydro-(4H)-pyran-4-ol. The benzoyl ester derivative was prepared as in Example 4 and analysed by chiral stationary phase HPLC also as described in Example 4. Analysis of the resolved sample indicated the optical purity to be 99% (2S, 4S), 1% (2R, 4R).

We claim:

1. A process of producing an optically active cis 2-substituted tetrahydropyran-4-ol which comprises stereospecifically hydrolysing an ester thereof with a stereospecific hydrolase.

2. A process according to claim 1 of producing an optically active 2-substituted tetrahydropyran-4-one which comprises stereospecifically hydrolysing an ester thereof with a stereospecific hydrolase, and further processing by oxidising the alcohol product to the corresponding ketone after separating it from the ester and/or separating the ester and alcohol or ketone products, hydrolysing the ester to the corresponding alcohol and oxidising the resulting alcohol to the corresponding ketone.

3. A process according to claim 1 of producing an optically active cis 2-substituted tetrahydropyran-4-ol which comprises producing a cis-racemic 2-substituted tetrahydopyran-4-ol by reacting but-3-ene-1-ol with an aldehyde of formula XCHO in which X is the desired 2-substituent of the pyranol in the presence of an acid, esterifying the racemic mixture using a stereospecific esterase or esterifying the racemic mixture optionally non stereospecifically and hydrolysing it with a stereospecific hydrolase.

4. A process according to claim 1 of producing an optically active 2-substituted tetrahydropyran-4-one which comprises producing a cis-racemic 2-substituted tetrahydropyran-4-ol by reacting but-3-ene-1-ol with an aldehyde of formula XCHO in which X is the desired 2-substituent of the pyranol in the presence of an acid, esterifying the racemic mixture using a stereospecific esterase or esterifying the racemic mixture optionally non stereospecifically and hydrolysing it with a stereospecific hydrolase and further processing by oxidising the resulting alcohol or an alcohol derived from the resulting ester to the corresponding ketone by hydrolysis.

5. A process as claimed in claim 1 in which the ester is separated from the alcohol.

6. A process as claimed in claim 1 in which the alcohol is further reacted to a desired product in the presence of the ester.

7. A process as claimed in claim 1 in which the alcohol stereoisomer is obtained stereospecifically.

8. A process as claimed in claim 1 which comprises a stereospecific esterification with the stereospecific hydrolysis.

9. A process as claimed in claim 1 in which the 2-substituent is an alkyl or substituted alkyl group.

10. A process as claimed in claim 8 in which the esterification is a transesterification with a vinyl ester.

11. A process as claimed in claim 1 in which the cis 2-substituted tetrahydropyranol is cis 2-methyl tetrahydropyranol or cis 2-ethyl tetrahydropyranol.

12. A process as claimed in claim 8 in which the esterification is carried out in the presence of a quantity of water not substantially greater than the minimum necessary to secure the optimum effectiveness of the enzyme.

13. A process as claimed in claim 1 in which the enzyme is derived from *Humicola lanuginosa*, Pseudomonas or *Candida antarctica*.

14. A process as claimed in claim 1 in which an alcohol is produced and converted to a ketone by reacting it with a strong oxidising agent in the presence of a strong acid and an inert organic solvent.

* * * * *